United States Patent
Widlund et al.

(12)

(10) Patent No.: US 6,210,388 B1
(45) Date of Patent: *Apr. 3, 2001

(54) METHOD FOR MANUFACTURING A PANTS-TYPE DIAPER OR SANITARY PANTY, AND SUCH AN ARTICLE

(75) Inventors: Urban Widlund, Mölnlycke; Anders Gustafsson, Billdal, both of (SE)

(73) Assignee: SCA Hygiene Products AB, Goteborg (SE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,297

(22) PCT Filed: Apr. 11, 1995

(86) PCT No.: PCT/SE95/00391

§ 371 Date: Oct. 4, 1996

§ 102(e) Date: Oct. 4, 1996

(87) PCT Pub. No.: WO95/27462

PCT Pub. Date: Oct. 19, 1995

(30) Foreign Application Priority Data

Apr. 12, 1994 (SE) .................................... 9401227

(51) Int. Cl.[7] .................................................. A61F 13/15

(52) U.S. Cl. .................. 604/390; 604/385.3; 604/391; 604/394; 156/66; 156/204; 156/217; 156/277

(58) Field of Search .................. 604/385.1, 385.2, 604/386, 387, 389–402, 365–366, 378, 385.21, 385.24, 385.29, 385.3; 156/161, 164; 186/229, 494, 495, 160, 163, 66, 91, 204, 217, 221, 226, 227, 443

(56) References Cited

U.S. PATENT DOCUMENTS

| 2,944,550 | * | 7/1960 | Magid | 604/366 |
| 3,874,386 | * | 4/1975 | Kozak | 604/390 |
| 3,901,239 | * | 8/1975 | Tritsch | 604/390 |
| 4,205,679 | * | 6/1980 | Repke et al. . | |
| 4,581,772 | | 4/1986 | Smith . | |
| 4,610,680 | | 9/1986 | LaFleur . | |

(List continued on next page.)

FOREIGN PATENT DOCUMENTS

| 0 320 991 | 6/1989 | (EP) . | |
| 947 346 | 1/1964 | (GB) . | |
| 1 356465 | 6/1974 | (GB) . | |
| 2 107 172 | 4/1983 | (GB) . | |
| 2 130 888 | 6/1984 | (GB) . | |
| 2 144 637 | 3/1985 | (GB) . | |
| 3176051 | * 7/1991 | (JP) | 604/385.2 |
| 4028363 | * 1/1992 | (JP) | 604/385.2 |
| 4161152 | * 6/1992 | (JP) | 604/385.2 |
| 5293135 | * 11/1993 | (JP) | 604/385.2 |
| 94/01070 | * 1/1994 | (WO) | 604/385.2 |

*Primary Examiner*—John G. Weiss
*Assistant Examiner*—K. M. Reichle
(74) *Attorney, Agent, or Firm*—Burns, Doane, Swecker & Mathis, L.L.P.

(57) ABSTRACT

A method of manufacturing an absorbent article in the form of a pants diaper or a sanitary panty starts from a flat blank which includes an elongated absorbent body (5) enclosed between two casing sheets (2, 9) which at opposing front and rear end parts of the absorbent body have side parts which extend laterally beyond the body on opposite sides thereof. The method includes the step of folding the blank about a transverse axis so that the end edges of the side parts lie edge-to-edge. The front and rear side parts of the blank which oppose one another in the folded state of the blank are joined together by a releasable and refastenable fastener (20). A pants diaper can be manufactured in accordance with this method.

10 Claims, 5 Drawing Sheets

U.S. PATENT DOCUMENTS

| | | |
|---|---|---|
| 4,610,681 | 9/1986 | Strohbeen et al. . |
| 4,617,022 * | 10/1986 | Pigneul et al. ................ 604/391 |
| 4,726,807 * | 2/1988 | Young et al. . |
| 4,735,622 | 4/1988 | Acuff et al. . |
| 4,895,569 * | 1/1990 | Wilson et al. ................ 604/386 |
| 5,074,854 | 12/1991 | Davis . |
| 5,085,658 * | 2/1992 | Mann et al. ................ 604/390 |
| 5,087,253 | 2/1992 | Cooper . |
| 5,324,279 * | 6/1994 | Lancasker et al. ................ 604/385.2 |
| 5,370,634 * | 12/1994 | Ando et al. ................ 604/393 |

\* cited by examiner

METHOD FOR MANUFACTURING A PANTS-TYPE DIAPER OR SANITARY PANTY, AND SUCH AN ARTICLE

BACKGROUND OF THE INVENTION

The present invention relates to a method of manufacturing an absorbent article in the form of a pants-type diaper or a sanitary panty, beginning with a flat diaper blank which comprises an elongated absorbent body enclosed between two casing sheets which at opposing front and rear end parts of the absorbent body have side parts which extend laterally beyond the absorbent body on both sides thereof, said method comprising the step of folding the blank about a transverse axis so that the end edges of said side parts will lie edge-to-edge. The invention also relates to articles manufactured in accordance with the method.

So-called all-in-one diapers are being replaced to an ever greater extent with pants-type diapers, or so-called training pants, for slightly older diaper-wearing children. Pants-type diapers have a number of good features. They fit well on the wearer, they are easy to put on and take off with the child in a standing position, they sit firmly in place after having been put onto a child, and conform to the anatomy of the child as the child moves, in a comfortable fashion. Moreover, pants-type diapers resemble conventional underpants and it is easy to understand how they shall be used, thereby in many instances enabling somewhat older diaper-wearing children to perform themselves the simple operations required in putting on the pant diaper. However, pants-type diapers, or training pants, also have certain drawbacks. They are difficult to change while the child is lying on his/her back and, when changing the pant diaper, require any garment that is worn on top of the pant diaper to be removed completely. Neither can a used pants-type diaper be rolled-up and sealed in the same manner as an all-in-one diaper. In addition, a dirty pant diaper which contains feces is liable to soil the wearer when removing the pant diaper.

OBJECTS AND SUMMARY

An object of the present invention is to provide an absorbent article in the form of a pants-type diaper or a sanitary panty which is not encumbered with the aforesaid drawbacks, while beginning with a pants-type diaper blank or a sanitary panty blank that has been manufactured in the same way as conventional diapers.

In accordance with the invention, this object is achieved with a method of the kind defined in the introduction which is characterized in that the side edges of the front and the rear side parts which mutually oppose one another in the folded state of the blank are joined together with the aid of a releasable and refastenable fastener means.

According to one preferred embodiment of the invention, one of two elements which include mutually complementary members of a releasable and refastenable fastener means, is attached to one of said front and rear side parts which mutually oppose one another in the folded state of the blank, while the other of said two elements is attached to the other of said side parts. In the case of this embodiment, the two elements are joined together and, prior to folding the blank, one of the elements is attached to one of the front and rear side parts that oppose each other when the blank is folded, while the other element is attached to the other side part in conjunction with folding the blank.

According to one variant of this embodiment of the inventive method, prior to folding the blank the two elements are attached in a mutually joined state to one of the front and rear side parts that oppose each other in the folded state of the blank, while the other element is attached to the other side part subsequent to folding the blank.

According to a second embodiment of the method, prior to folding the blank, the two elements are attached to respective side parts while spaced apart, whereafter the two elements are joined to one another in the final stage of folding the blank.

According to a third embodiment of the method, the two elements are attached in a mutually joined state after folding the blank.

The invention also relates to an absorbent article in the form of a pants-like diaper or sanitary panty, said article comprising an elongated absorbent body which is enclosed between two casing sheets which extend laterally outside the absorbent body on both sides thereof at the mutually opposing front and rear end parts of said body. The article is characterized in that the side edges of mutually opposing front and rear side parts are joined together by a releasable and refastenable fastener means.

According to one preferred embodiment of the article, the releasable and refastenable fastener means is comprised of mutually complementary members of two fastener elements, of which one is attached to the front side part and the other to the rear side part. The mutually complementary members may have the form of buttons and button holes, hooks and eyes, beads and grooves, or the male and female parts of self-fastening bands, e.g. VELCRO tapes.

According to one variant, the fastener means has the form of an adhesive coating.

BRIEF DESCRIPTION OF THE DRAWINGS

The invention will now be described in more detail with reference to the accompanying drawings, in which.

DETAILED DESCRIPTION OF THE PREFERRED EMBODIMENTS

Figure 1:
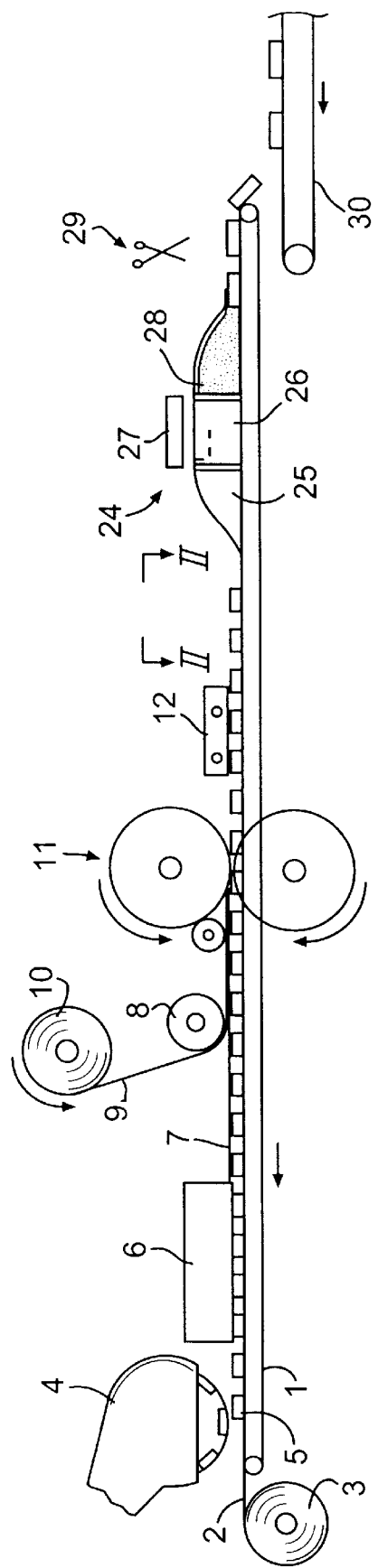
FIG. 1 illustrates schematically plant machinery for manufacturing an inventive pants-type diaper by means of an inventive method.

FIG. 1 illustrates schematically plant machinery for manufacturing pants-type diapers, including a conveyer path 1 by means of which casing material 2 taken from a storage reel is conveyed from left to right in FIG. 1. Located downstream of the reel 3 is a device 4 which lays absorbent bodies 5 at regular intervals on the underlying web of casing material 2. Located downstream of the device 4 is a device 5 which lays elastic elements in a specific pattern onto or immediately above the web of casing material 2. These elastic elements, of which one 7 is shown schematically in FIG. 1 and which are preferably comprised of elastic threads or ribbons, form the waist and leg elastic of the manufactured pants-type diaper. Located downstream of the device 6 are guide rollers 8 which function to guide a second web of casing material 9 from roll 20 onto the first web 2, while downstream of the guide rollers 8, there is located a device 11 which brings the webs of casing material together and fastens the webs to one another at those parts thereof which lie outside the absorbent bodies 5. The plant machinery hitherto described functions in the same way as the plant machinery used to manufacture conventional all-in-one diapers and the composite product leaving the device 11 will be comprised of a continuous string of pants-type diaper blanks which, similar to the all-in-one diapers produced in conventional plants, includes an absorbent body which is enclosed between the two casing sheets and also elastic elements. At this stage of manufacture, the pants-type diaper blank differs from a typical diaper blank mainly in that the waist elastic has a different form to the waist elastic with which a diaper blank may be provided, as will be made more apparent in the following. The devices 4, 6, 8 and 11 are preferably known devices suitable for producing a pants-type diaper blank of the aforesaid kind. Since a detailed description of the construction of these devices is not needed to acquire an understanding of the invention, the devices will not be further described.

Located downstream of the device 11 is a device 12 which functions to attach fastener elements 13 to the underlying moving web of mutually connected blanks. The device 12 will preferably include plungers or the like that are operative in pressing glue-coated fastener elements 12 against the casing sheet 9.

Figure 2:
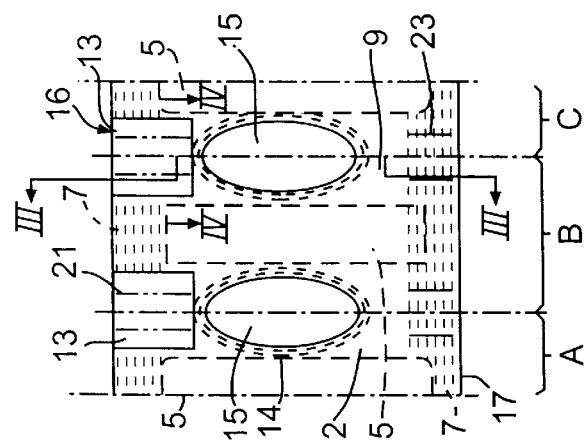
FIG. 2 illustrates from above part of the material web shown in FIG. 1, in the manufacturing stage immediately prior to folding and joining the pants-type diaper blanks to form pants-type diapers.

FIG. 2 illustrates from above a section of the web of mutually joined blanks subsequent to the web exiting from the device 12. The section illustrated in the Figure includes a complete pants-type diaper blank B and parts of two mutually adjacent blanks A and C. As will be seen from the Figure, the device 6 lays-out across the blank a plurality of elastic threads 7 which extend sequentially in the transverse direction of the blank and which form the waist elastic of a manufactured pants-type diaper, and also lays-out around openings 15 cut from the web elastic threads 14 which form the leg elastic of a manufactured pants-type diaper. The openings are preferably cut from the web when joining the casing sheets together with the aid of some appropriate means, for instance by means of a punch included in the device 11 or located immediately downstream thereof.

The pants-type diaper blanks A, B, C include a front edge 16, a rear edge 17 and a central part which is delimited by the mutually opposing long edges of the absorbent body 5 and the extensions of said long edges, front side parts on both sides of the central part and the rear side parts, these side parts being delimited by the front edge 16 and the rear edge 17 respectively, the openings 15 lying on respective edges of the central part, and the imaginary separation lines between the individual blanks A, B and C, as illustrated in FIG. 2 in dash-dotted lines.

Figure 4:
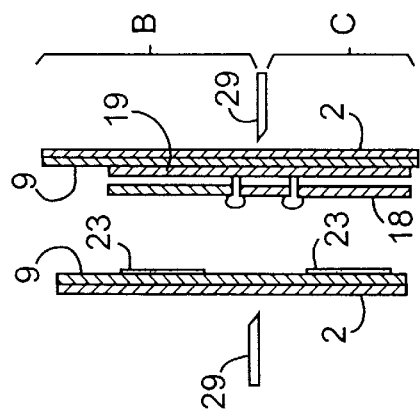
FIG. 4 is a cross-sectional view taken on the line IV—IV in FIG. 2 and illustrates schematically a final stage in the manufacture of the pants-type diaper.
Figure 3A:
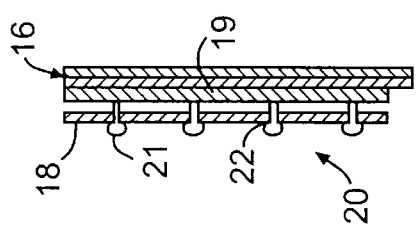
FIG. 3A is an enlarged view of part of the section shown in FIG. 3.
Figure 5:
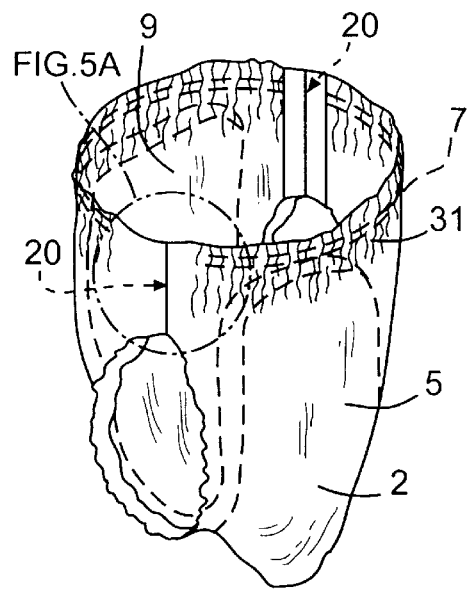
FIG. 5 is a perspective view of a pants-type diaper produced by means of the inventive method.
Figure 5A:
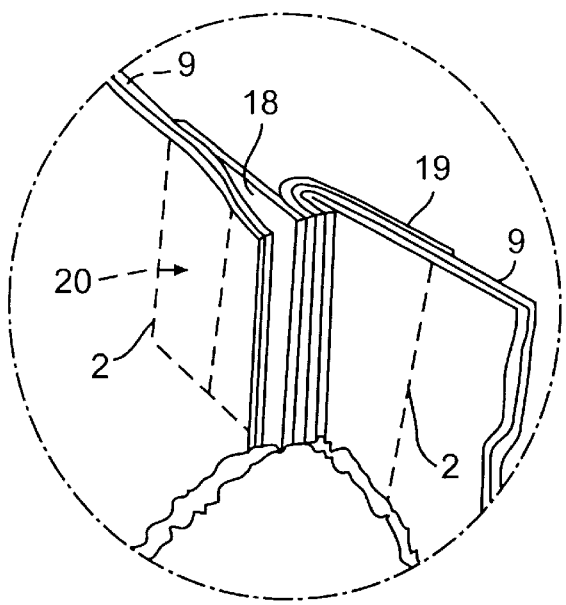
FIG. 5A is an enlarged part of the section shown in FIG. 5.

The fastener elements 13 as best shown in FIG. 5A, are comprised of two similarly shaped rectangular pieces 18, 19 of flexible material which are joined together by two releasable and refastenable fastener means 20. As will best be seen from FIGS. 3A and 4, each of the fastener means 20 is comprised of a row of projections 21 which extend from the fastener piece 19 and pass through a row of through-penetrating openings 22 formed in the fastener piece 18 and complementary in shape to a respective projection 21. The fastener elements 13 are placed in the front side parts of the blanks, symmetrically in relation to the imaginary blank separation lines, so that the two fastener means will lie on opposite sides of said lines.

Figure 3:
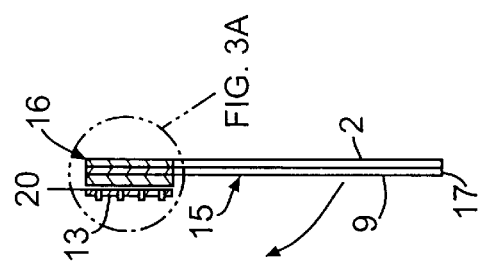
FIG. 3 is a sectional view taken on the line III—III in FIG. 2.

Pants-type diapers are produced from the blanks shown in FIGS. 2 and 3, simply by folding the blanks in the direction indicated by the arrow in FIG. 3, so that the edges 16 and 17 will lie opposite one another, and by fastening the casing sheet 9 to the fastener elements 13 in conjunction therewith. Glue beads 23 are suitably applied to the pieces 18 of the fastener elements 13 in conjunction with bringing the edges 16, 17 together. Naturally, the glue beads 23 may instead be applied to the casing sheet 9 on the rear side parts prior to folding the blanks, as indicated in FIGS. 2 and 4.

The plant illustrated in FIG. 1 includes downstream of the device 11 a device 24 by means of which the web of blanks is folded together and the front and rear side parts of the blanks are joined to one another. The device 24 may include fixed guide means 25 having mutually converging side walls, plunger means 26 which intermittently press the rear side parts of the blanks against the front side parts thereof, applicator means 27 for applying glue to the fastener elements 13 or to the rear side parts, and fixed guide means 28 having side walls which extend successively from a vertical to a horizontal position.

The web moving through the guide means 28 is thus comprised of a string of mutually joined pants-type diapers which after exiting from the guide means 28 are separated from one another by means of an appropriate cutting tool 29 and conveyed by suitable conveying means 30 to a packaging station in which they are packaged as individual pants-type diapers.

FIG. 4 illustrates part of the web in the final stage of the folding operation, this Figure also showing the cutting tool 29 schematically in order to indicate that the individual diapers can be cut from the web in conjunction with fastening the rear side parts of the blank to the piece 18 of the fastener element 13, as will be understood.

It will also be understood that the fastener arrangement can be attached to the web in ways other than by gluing, for instance by heat-welding or ultrasonic welding.

FIG. 5 is a perspective view of a pants-type diaper manufactured by the aforedescribed method. A pants-type diaper is intended to be put on in the same way as a pair of underpants, and is characterized by an elastic waist part which can be stretched so as to enable the pant diaper to be easily drawn over the wearer's hips when putting on and removing the pant diaper, and which is so elastic as to ensure that when worn the pant diaper will be held securely in place by the contraction forces exerted by the elastication in the waist part of the pant diaper. In order to fulfill these functional requirements while, at the same time, limiting the number of product sizes required, the pant diaper will preferably have a stretch which is greater than 80%, i.e. it shall be possible to stretch the waist part to an extent which corresponds to 1.8 times the circumference of the waist part of a pants-type diaper in a relaxed state. When the pant diaper is worn, the combined contraction force in the waist part, i.e. the sum of the forces exerted by the elastic provided in the front part, the rear part and the side parts of the pant diaper, will preferably exceed 3 N.

The pants-type diaper illustrated in FIG. 5 is suitably constructed in the same way as the pants-type diaper described in Swedish Patent Application No. 9200663-4, and includes an absorbent body 5 enclosed between the inner and an outer casing sheet, 9 and 2, respectively. The inner casing sheet 9 is liquid-permeable and is comprised, for instance, of nonwoven material compiled from fibres of polyethylene, polypropylene, polyester or mixtures thereof. Vicose fibres may also be used. It is also conceivable to form the inner casing sheet from a perforated plastic sheet, for instance a perforated polyethylene sheet. The outer casing sheet 2 is liquid-impermeable or at least hydrophobic and may, for instance, comprise a sheet of polyethylene or nonwoven material which has been coated with or laminated with polyolefins, so as to be made liquid-impermeable or at least hydrophobic. For aesthetic and psychological reasons, the outer casing sheet 2 may be comprised of two layers, an inner liquid-impermeable layer and a layer of fabric-like material disposed outside the inner layer. The wearer will then see and feel the diaper as a fabric garment rather than as a plastic garment. When the outer casing sheet has this letter construction, it is not necessary for the liquid-impermeable sheet to have the same extension as the fabric-like sheet, but may be smaller than said sheet, for instance liquid-impermeable casing material can be omitted from the side parts of the diaper.

The absorbent body 5 may contain cellulose fluff pulp with or without an admixture of particles of so-called superabsorbent material or thermoplastic melt fibres, and may be comprised of one or more layers.

The waist part 31 of the pants-type diaper includes a plurality of sequentially mounted elastic threads 7, as also shown in FIG. 2, each of which extends transversely around the circumference of the center part. In this way, there is formed a relatively broad elastic waist part. As will be understood, elastic ribbons, bands or the like may be used instead of elastic threads, or other elastically stretchable material can be used, such as elastically stretchable plastic film, an elastically stretchable nonwoven material, or like material.

Similar to a pair of underpants, the pants-type diaper illustrated in FIG. 5 has a waist opening and two leg openings, which are provided with leg elastic in a conventional manner. The pant diaper is put on by inserting the legs of the wearer through the leg openings and then drawing the pant diaper up over the wearer's hips. The contraction forces exerted by the elastic elements at the waist opening, i.e. at the uppermost part of the waist part 31, are preferably greater than the contraction forces exerted in the remainder of the waist part. This will ensure that the pant diaper remains seated in its intended position, even when the absorbent body has absorbed urine to a point of saturation.

According to the invention, the front and the rear side parts of the pant diaper are joined together by means of a releasable and refastenable fastener means 20. When the fastener means 20 is released, the pant diaper can be removed and changed without needing to remove completely any trousers or like garment worn outside the pant diaper, since the rear part or the front part of the pant diaper can then be withdrawn between the wearer's legs. A replacement pants-type diaper can then be placed on the wearer, by releasing the fastener means 20 and inserting the front part or the rear part of the replacement pant diaper between the wearer's legs. The side parts are then fastened together, by refastening the fastener means 20, whereafter the pant diaper is drawn up to its correct position in the same way as a pair of underpants, unless this has already been done in conjunction with refastening the fastener means.

Figure 6:
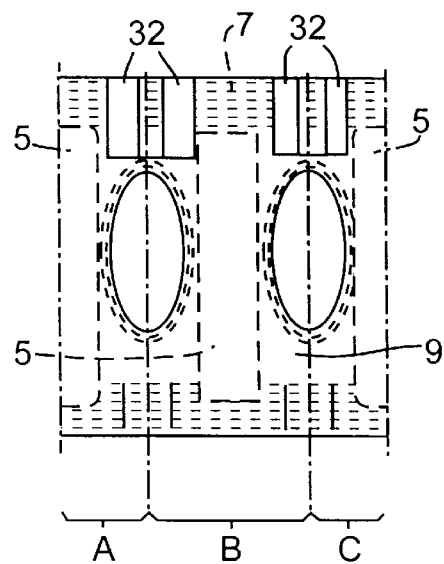
FIGS. 6–8 are views similar to the views of FIGS. 2, 4 and 5 respectively and show the manufacture of a second embodiment of an inventive pants-type diaper.
Figure 7:
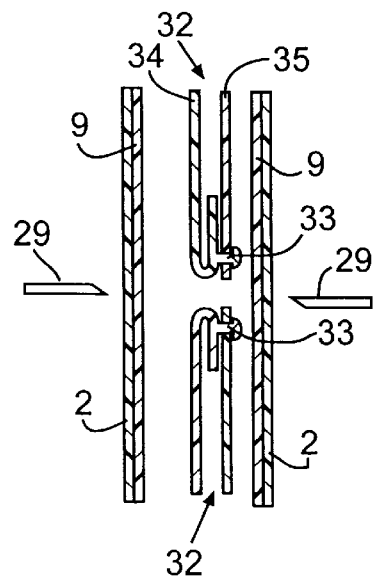
Figure 8A:
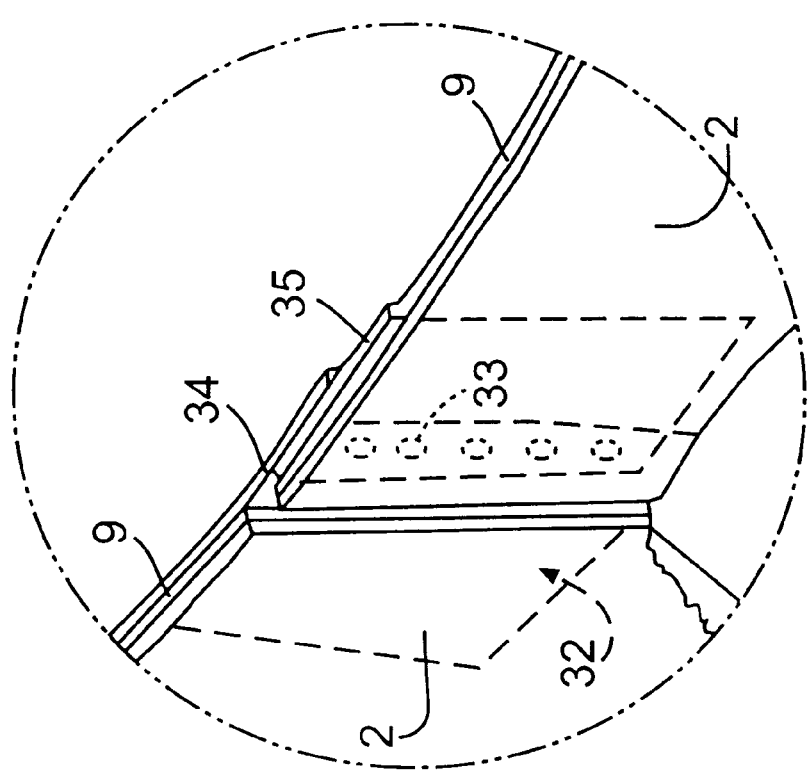
FIG. 8A is an enlarged part of the section shown in FIG. 8.
Figure 8:
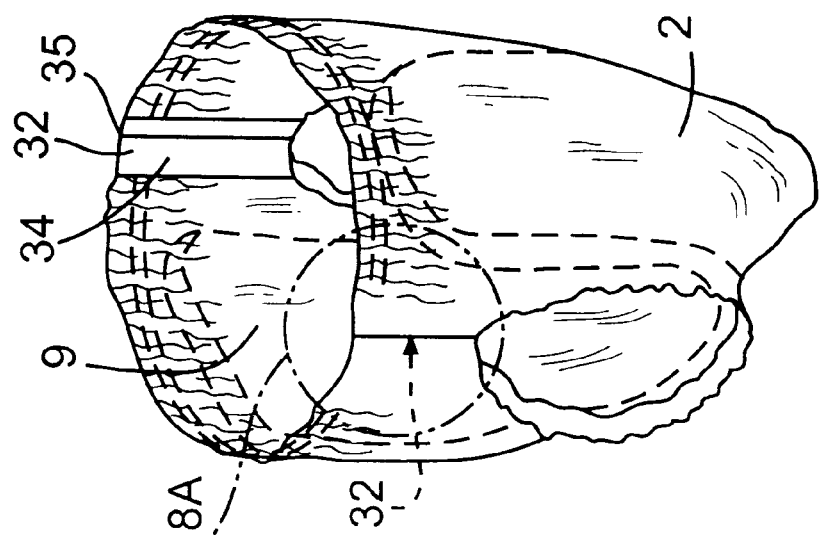

FIGS. 6–8 are views which correspond to the respective views of FIGS. 2, 4 and 5, and illustrates a second embodiment of the invention. The second embodiment of the inventive pants-type diaper is manufactured in the same way as that earlier described, up to the point of attaching the fastener elements to the casing sheet 9. Those elements in FIGS. 6–8 which find correspondence in FIGS. 1–5 have been identified with the same reference signs. The embodiment illustrated in FIGS. 6–8 differs from the earlier described embodiment in that instead of one fastener element 13 which includes two fastener means 20, there are attached two fastener elements 32 each of which includes one fastener means 33 on either side of each imaginary blank separating line between the mutually adjacent pants-type diaper blanks A–C of a mutually joined string of blanks. In other respects, a pants-type diaper according to this second embodiment is manufactured in the same way as that described with reference to FIGS. 1–5. The fastener elements 32 of this embodiment as best shown in FIG. 8A, also include two flexible pieces 34, 35 which are mutually joined by fastener means 33 similar to the fastener means 20 of the first embodiment. The end part of the flexible piece 43 that contains the row of projections is folded-in against the remainder of said piece. The fold or pleat obtained when folding-in said end part will be unfolded or lifted when wearing a pants-type diaper according to this second embodiment of the invention, as illustrated in FIG. 8, which is a perspective view of one such diaper.

Figure 9:
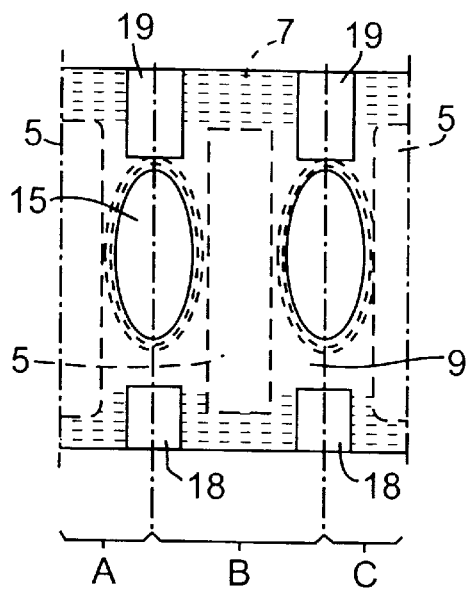
FIGS. 9 and 10 are views similar to the views of FIGS. 2 and 4 respectively and illustrate a third embodiment of the manufacture of an inventive pants-type diaper.
Figure 10:
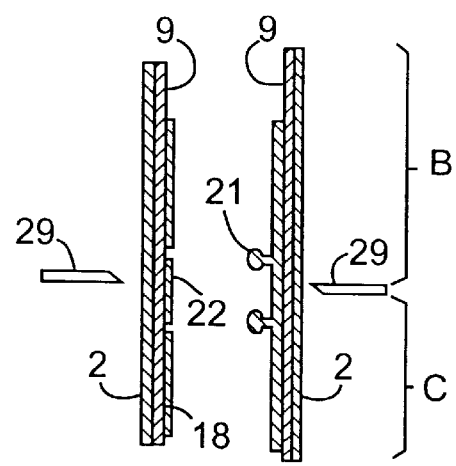

FIGS. 9 and 10 illustrate a third exemplifying embodiment of a method of manufacturing an inventive pants-type diaper. The views shown in FIGS. 9 and 10 correspond to the views shown in FIGS. 2, 4 and 6, 7, respectively. The diaper according to this third embodiment of the invention is manufactured in the same way as that earlier described, up to the point of applying the fastener elements to the casing sheet 9. Those elements in FIGS. 9 and 10 which find correspondence in FIGS. 1–5 have been identified by the same reference signs. The third embodiment differs from the first embodiment in that the fastener elements 13 are applied by the device 12 with the pieces of material 18, 19 separate from one another, i.e. with the fastener means 20 loosened. In this regard, the pieces 18 are applied to the front side parts, whereas the pieces 19 are applied to the rear side parts. When subsequently folding the web, the projections 21 of each fastener means 20 are pressed into the openings 22, whereafter manufactured pants-type diapers having the configuration shown in FIG. 5 are produced by cutting with the aid of the tool 29.

All of the aforedescribed, illustrated fastener means are configured so that an opened pants-type diaper can only be refastened when the separate parts of the side parts are placed in the same positions as those occupied prior to opening the pant diaper. This ensures that the good fit afforded by a pants-type diaper will be retained after the pant diaper has been refastened. In this way, the absorbent body of a refastened pant diaper will also lie in its intended position in relation to the anatomy of the wearer, which is important in ensuring that no leakage will occur. Furthermore, the absorbent bodies of present-day diapers and sanitary napkins are to an ever increasing extent configured to receive body fluid within particularly defined areas of the absorbent body, and the function of such bodies can be jeopardized when the fluid is received outside these areas. The waist elastic of pants-type diapers and sanitary panties are also dimensioned with a starting point from a specific circumferential length in the natural state of the product, i.e. when no load is exerted thereon, and consequently it is important to the intended function of the waist elastic that its circumferential length is retained after refastening an opened pants-type diaper or sanitary panty. It will be understood, however, that the fastener means need not have the illustrated configuration and that other types of fastener means can be used within the scope of the invention, such as self-fastening or hook and loop means, e.g. VELCRO® tape, or adhesive applications that have a relatively large extension in the circumferential direction of the pant diaper and also in its height direction, i.e. a direction at right angles to its circumference. However, it is convenient in such casings to mark or indicate on the casing sheets how the separate parts of these side parts shall be fastened together. Preferably, it will be apparent how the parts shall be related to one another in a vertical or height direction, since it is particularly important with respect to the fit of the pant diaper that any deviations in the vertical position of the separate parts of said side parts are small. When using self-fastening tape or adhesive fastener means, it will preferably be ensured that these fastener means are so disposed as to be subjected solely to shear forces when the pant diaper is worn. The second embodiment of the fastener means described hitherto is preferred for this reason.

The aforedescribed method of fastening the tapes to the side parts of a pants-type diaper blank can be applied when the absorbent bodies are placed transversely to or when placed longitudinally to the direction of web movement in the manufacture of pants-type diapers, but with the difference that in the longitudinal production of pant diapers, it is necessary to cut the individual blanks from the string of blanks prior to folding the rear side parts onto the front side parts.

When the blanks are advanced as individual blanks, fastener elements of the aforementioned kind having closed fastener means can be applied to the casing sheet 2 instead of the casing sheet 9, by first fastening a free end of the fastener elements to one of the front side parts of the blank and thereafter folding the blank. The fastener elements are then folded-in over the rear side parts of the folded blank and fastened thereto. As will be understood the flat or non-folded fastener elements can also be attached to the inner casing sheet 9, on the front side parts of the individual flat blank and thereafter folding the blank and then the fastener elements, whereupon the fastener elements fasten to the inner surfaces of the front side parts and to the outer surfaces of the rear side parts. The fastener elements can also be applied after having folded the individual blanks, for instance by passing the edges of the blank side parts folded against one another between the free edges of a folded fastener element and then pressing the edges of the fastener element firmly against the side parts with the aid of an externally applied force.

It will be noted in this regard that the fastener elements may, of course, be fastened to the front and the rear side parts in a reverse order to that described, i.e. are first attached to the rear side parts and then to the front side parts.

According to a variant of the method described with reference to FIGS. 6–8, the folded fastener elements 32 can be passed in between the front and rear side parts during the final stage of folding the blanks, and fastened to the blanks in a single stage.

Figure 11:
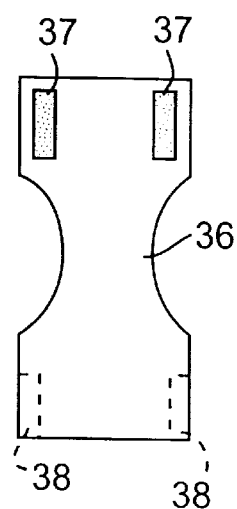
FIGS. 11 and 12 illustrate a fourth embodiment of the manufacture of an inventive pants-type diaper.
Figure 12:
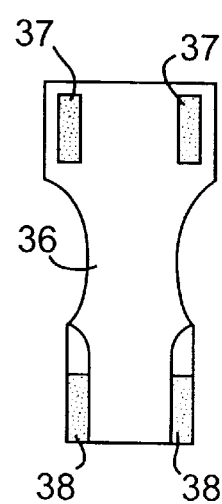

Alternatively, the side parts of the individual pants-type diaper blanks may be folded prior to folding the blank or in conjunction therewith, instead of folding the fastener elements. An example of this is illustrated in FIGS. 11 and 12. These Figures illustrate schematically a pants-type diaper blank 36 in which one part 37 of a fastener element is comprised of two mutually coacting parts 37, 38 which are fastened respectively to the inner surface of the blank at the front side parts thereof, while the other part 38 of the fastener elements is fastened to the outer surface of the blank at the rear side parts thereof. FIG. 11 shows the blank 36 from above, subsequent to having cut the blank from a web of mutually joined blanks. The parts 38 of the fastener elements are preferably attached to the outer casing sheet in an initial stage of manufacture, prior to mounting absorbent bodies, elastic elements and an inner casing sheet. In order to produce a finished pants-type diaper from a blank that has the configuration illustrated in FIG. 11, those parts of the rear side parts of the blank 36 that contain the parts 38 of the fastener elements are folded against the inner surface of the blank, so as to provide a blank 36 having the configuration shown in FIG. 12. The blank is then folded so that the front and the rear side parts thereof are placed edge-to-edge, and the coacting parts 37, 38 are pressed firmly against one another. The parts 38 include fastener elements of the earlier described kind, and self-fastening or hook and loop tapes and adhesive tapes may also be used, since the resultant connection or join will be subjected essentially to shear forces when the diaper is worn. It will be understood that the parts 38 may be applied after folding-in the rear side parts of the blank, instead of in an initial stage of manufacture.

Although the described and illustrated exemplifying embodiments of the invention are directly solely to pants-type diapers, it will be understood that the invention can also be applied to sanitary panties, i.e. panties in absorbent bodies for absorbing menstrual fluids or light incontinence discharges are integrated.

It will also be understood that the described and illustrated exemplifying embodiments can be modified within the scope of the invention. For instance, the absorbent body may have a form different to that described and may include several layers, which in turn means that the described plant for manufacturing pants-type diapers in accordance with the invention will be modified correspondingly.

Furthermore, the pants-type diaper blanks can be folded and the front and rear side parts of the blanks brought together with the aid of means other than those described. The individual pants-type diapers can be cut from the continuous web of blanks in conjunction with bringing the front and rear side parts of the blanks together, instead of in a separate following stage. The invention is therefore restricted solely by the scope of the following claims.

What is claimed is:

1. A method of manufacturing an absorbent article in the form of a pants diaper or a sanitary panty, said method comprising the steps of:

providing a web of a plurality of mutually joined flat blanks, each of said plurality of blanks including an elongated absorbent body enclosed between two casing sheets which at mutually opposing front and rear end parts of the absorbent body have side parts that extend laterally beyond said body on both sides thereof, the side parts having end edges;

providing a releasable and refastenable fastener having two elements;

mounting one of the two elements which include mutually complementary members of the releasable and refastenable fastener on the inside of the side parts of one of the front and rear end parts of each said blank;

mounting a second of the two elements on the inside of the side parts of the opposing other of the front and rear end parts so as to enable connection of the opposing side parts;

folding said web of mutually joined blanks about a traverse axis so that the end edges of said side parts of each said blank lie edge-to-edge, joining together the front and rear side parts which oppose one another in a final stage of folding of said web with said releasable and refastenable having two elements, said joining step including fastening the two elements of the releasable and refastenable fastener to one another and thereby connecting the opposing side parts and thereby forming a completed circumferential waist and defined leg openings in each said blank, thus forming a web of mutually joined, fastened, folded blanks, and thereafter separating the mutually joined blanks from each other by cutting individual ones of said absorbent article from the web of mutually joined, fastened, folded blanks.

2. A method of manufacturing an absorbent article in the form of a pants diaper or a sanitary panty, said method comprising the steps of:

providing a web of mutually joined flat blanks, each of said plurality of blanks including an elongated absorbent body enclosed between two casing sheets which at mutually opposing front and rear parts of the absorbent body have sides parts that extend laterally beyond said body on both sides thereof, the side part having end edges;

providing a releasable and refastenable fastener having two elements;

mounting one of the two elements, with the two elements mutually fastened together, on the inside of the side parts of one of the front and rear end parts of each said blank that oppose one another after a folding of said web, folding said web of mutually joined blanks about a transverse axis so that the end edges of said side parts of each said blank lie edge-to-edge, and in conjunction with folding said web of mutually joined blanks, joining together the front and rear side parts of each said blank which oppose one another after folding of said web with the releasable and refastenable fastener having two elements, said joining step including mounting the other element of the releasable and refastenable fastener, with the two elements mutually fastened together, on the inside of the side parts of the opposing other of the front and rear end parts of each said blank, thereby forming a completed circumferential waist and defined leg openings in the blank, and thereafter separating the mutually joined blanks from each other by cutting, thereby forming individual ones of said absorbent article from the web of mutually joined folded blanks.

3. An absorbent article in the form of a pants diaper or sanitary panty having a complete circumferential waist and defined leg openings directly after manufacture, said article comprising:

an elongated absorbent body enclosed between two casing sheets, at opposing front and rear end parts of the absorbent body, said casing sheets have side parts which extend laterally beyond said absorbent body on both sides thereof, the side parts of the front and rear end parts having the same lateral extension, and the opposing front and rear side parts being joined together with releasable and refastenable fasteners, respectively, each of said releasable and refastenable fasteners being comprised of mutually complementary members of two elements, of which one of the two elements is fastened to the inside of the front side part and a second of the two elements is fastened to the inside of the rear side part, a circumferential waist opening including waist elastics, and a pair of defined leg openings including elastic.

4. An article according to claim 3, wherein the mutually complementary members are comprised of buttons and button holes.

5. An article according to claim 3, wherein the mutually complementary members are comprised of hooks and eyes.

6. An article according to claim 3, wherein the mutually complementary members are comprised of beads and grooves.

7. An article according to claim 3, wherein the mutually complementary members are comprised of male and female parts of a self-fastening tape.

8. An article according to claim 3, wherein one of the mutually complementary members is provided with an adhesive coating.

9. An article according to claim 3, wherein the mutually complementary members are comprised of projections on one of the two elements and cooperating through-openings on the other of the two elements.

10. An article according to claim 3, wherein the circumferential waist is elasticized, said elasticized waist stretching over buttocks of a wearer when the absorbent article is pulled onto the wearer, said releasable and refastenable fasteners maintaining said fastened position when said elasticized waist stretches over the buttocks of the wearer.

* * * * *